(12) United States Patent
Taylor

(10) Patent No.: US 9,387,015 B2
(45) Date of Patent: Jul. 12, 2016

(54) VERTEBRAL OSTEOSYNTHESIS EQUIPMENT

(71) Applicant: MEDICREA INTERNATIONAL, Neyron (FR)

(72) Inventor: Benjamin Taylor, Tring (GB)

(73) Assignee: MEDICREA INTERNATIONAL, Neyron (FR)

( * ) Notice: Subject to any disclaimer, the term of this patent is extended or adjusted under 35 U.S.C. 154(b) by 0 days.

(21) Appl. No.: 14/510,538

(22) Filed: Oct. 9, 2014

(65) Prior Publication Data

US 2015/0025576 A1    Jan. 22, 2015

Related U.S. Application Data

(63) Continuation of application No. PCT/IB2013/052626, filed on Apr. 2, 2013.

(30) Foreign Application Priority Data

Apr. 11, 2012    (FR) ...................................... 12 53284

(51) Int. Cl.
*A61B 17/70*    (2006.01)

(52) U.S. Cl.
CPC ......... *A61B 17/7055* (2013.01); *A61B 17/7002* (2013.01); *A61B 17/704* (2013.01); *A61B 17/7035* (2013.01); *A61B 17/7041* (2013.01); *A61B 17/7049* (2013.01)

(58) Field of Classification Search
CPC ....................................... A61B 17/70–17/8095
See application file for complete search history.

(56) References Cited

U.S. PATENT DOCUMENTS

| | | | | |
|---|---|---|---|---|
| 4,887,595 A | * | 12/1989 | Heinig et al. | 606/254 |
| 5,000,165 A | * | 3/1991 | Watanabe | 606/250 |
| 5,000,166 A | * | 3/1991 | Karpf | 606/250 |
| 5,041,113 A | * | 8/1991 | Biedermann et al. | 606/288 |
| 5,127,912 A | * | 7/1992 | Ray et al. | 606/250 |
| 5,306,275 A | | 4/1994 | Bryan | |
| 5,360,429 A | * | 11/1994 | Jeanson et al. | 606/250 |
| 5,380,324 A | * | 1/1995 | Muller et al. | 606/256 |
| 5,397,363 A | * | 3/1995 | Gelbard | 606/250 |

(Continued)

FOREIGN PATENT DOCUMENTS

| | | |
|---|---|---|
| EP | 1600112 A1 | 11/2005 |
| WO | 98/55038 A1 | 12/1998 |

OTHER PUBLICATIONS

International Search Report for corresponding PCT Application No. PCT/IB2013/052626, mailed Jun. 25, 2013.

*Primary Examiner* — Jan Christopher Merene
*Assistant Examiner* — Steven Cotroneo
(74) *Attorney, Agent, or Firm* — Myers Wolin, LLC

(57) ABSTRACT

This equipment comprises at least one connecting bar and at least one sacrum anchor assembly (1-3, 5). According to the invention, each sacrum anchor assembly comprises two sacral anchor screws (1, 2), a link assembly (3) including: a sacral connecting part (10) assembled to a sacral anchor plate (11) with polyaxiality, i.e. having possible multi-directional tilting relative to the said first screw (1), and possible pivot relative to the said sacral anchor plate (11); two nuts (5) able to be screwed onto the said shanks (9) of the said first and second screws (1, 2), a first nut (5) is able to clamp this part (10) against a bearing surface (8) formed in the said first screw (1), for tilt and pivot immobilisation of this part (10) relative to the said sacral anchor plate (11).

7 Claims, 5 Drawing Sheets

(56) References Cited

U.S. PATENT DOCUMENTS

| | | | |
|---|---|---|---|
| 5,735,853 A * | 4/1998 | Olerud | 606/71 |
| 5,947,968 A * | 9/1999 | Rogozinski | 623/17.16 |
| 6,565,569 B1 * | 5/2003 | Assaker et al. | 606/250 |
| 7,131,972 B2 * | 11/2006 | Mazda et al. | 606/250 |
| 2004/0006342 A1 * | 1/2004 | Altarac et al. | 606/61 |
| 2006/0064091 A1 * | 3/2006 | Ludwig et al. | 606/61 |
| 2007/0161987 A1 * | 7/2007 | Capote et al. | 606/61 |
| 2009/0062915 A1 * | 3/2009 | Kohm et al. | 623/17.11 |
| 2009/0093843 A1 * | 4/2009 | Lemoine et al. | 606/246 |
| 2010/0174315 A1 * | 7/2010 | Scodary et al. | 606/248 |

* cited by examiner

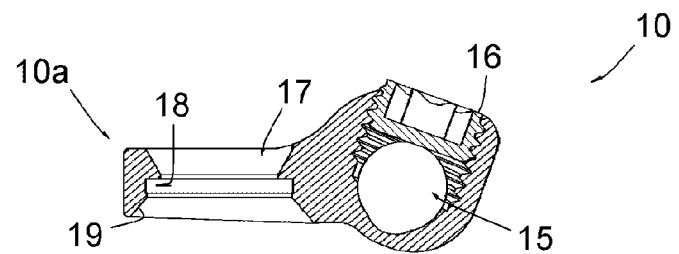
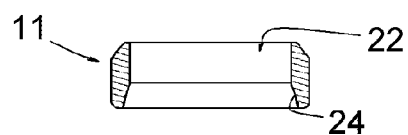
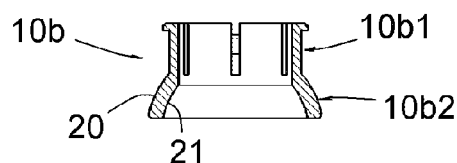
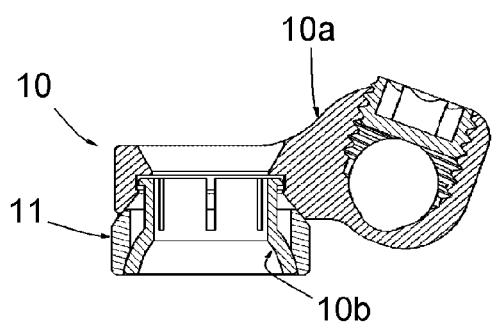
FIG. 5
FIG. 6
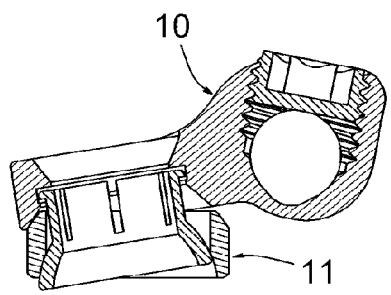
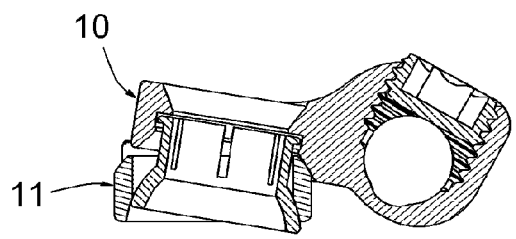
FIG. 7
FIG. 8

VERTEBRAL OSTEOSYNTHESIS EQUIPMENT

CROSS REFERENCE TO RELATED APPLICATIONS

This application is a continuation of International Patent Application No. PCT/IB2013/052626, filed Apr. 2, 2013, now pending, which claims foreign priority to French Patent Application No. FR 12 53284, filed Apr. 11, 2012, now pending, the disclosure of which are herein wholly incorporated by reference.

TECHNICAL FIELD

The present invention concerns vertebral osteosynthesis equipment.

BACKGROUND OF THE INVENTION

It is well known to obtain correction of the position of a portion of the spine, or the immobilisation of said portion, by means of vertebral osteosynthesis equipment comprising rigid connecting bars able to connect several vertebrae together, bone anchoring members (hooks or pedicle screws) to obtain anchoring of these connecting bars onto the vertebrae, and connecting parts for rigid connection of the connecting bars to these bone anchoring members.

The treated vertebral portion is frequently the lumbar portion. If it is the lumbar portion of the spine that is treated, the surgeon may wish to anchor the equipment onto the sacrum.

Vertebral osteosynthesis equipments exist which comprise plates to anchor the equipment to the sacrum.

These equipments have the disadvantage however of not always allowing anchoring to the sacrum of high resistance. Much demand is placed on the anchor screws anchored to the first vertebra of the sacrum through movements of the patient, and the cortical bone at this point is of relatively narrow thickness not allowing very strong anchoring. In addition, this bone may be of poor quality.

A further disadvantage of these existing equipments is the fact that the anchoring to the sacrum made possible by these equipments may lead to undesirable major stress being applied to the fifth and fourth lumbar vertebrae.

Various existing equipments are illustrated in the publications of patent applications No EP 1 600 112 A1, U.S. Pat. No. 5,306,275 A and WO 98/55038.

OBJECTS OF THE INVENTION

It is therefore an objective of this invention to provide equipment with which it is possible to obtain strong sacrum anchoring, including when the bone is of poor quality.

A further objective of the invention is to provide equipment eliminating the risk of applying undesirable stress onto the fifth and fourth lumbar vertebrae.

SUMMARY OF THE INVENTION

According to the invention, the equipment concerned comprises:
  at least one connecting bar able to link several vertebrae;
  bone anchoring members suitable for anchoring of this connecting bar onto the vertebrae;
  connecting parts allowing the connecting bar to be connected to these bone anchoring members; and
  at least one sacrum anchor assembly; each sacrum anchor assembly comprising:
    two sacral anchor screws, the first intended to be implanted in the first vertebra of the sacrum and the second intended to be implanted in the second vertebra of the sacrum, each screw comprising a threaded base portion intended to be inserted in the corresponding vertebra, a bearing surface and a threaded proximal shank, the shape of said bearing surface of the said first screw being a portion of a sphere;
    a link assembly including:
      a sacral connecting part comprising an orifice for engaging on said connecting bar, an orifice for engaging on the shank of said first screw and a bearing surface shaped as a portion of a sphere able to bear upon the said bearing surface formed in the said first screw, this bearing being obtained via polyaxiality i.e. the sacral connecting part having possible multi-directional tilting relative to the said first screw;
      a sacral anchor plate comprising a first orifice intended to engage on the shank of the said first screw and a second orifice intended to engage on the said shank of the said second screw;
      means for assembling the said sacral connecting part to the said sacral anchor plate, this assembling being such that the said orifice for engaging on the shank lies coaxial to the said first orifice, the said sacral connecting part is connected to the said sacral anchor plate in a direction parallel to the axis of these holes, and the said sacral connecting part is able to pivot relative to the said sacral anchor plate along this same axis;
    two nuts, a first nut able to be screwed onto the said shank of the said first screw and to bear against the said sacral connecting part so as to clamp this sacral connecting part against the said bearing surface formed in the said first screw, for tilt and pivot immobilisation of this part relative to the said sacral anchor plate, and the second nut able to be screwed onto the said shank of the said second screw and to bear against the said sacral anchor plate so as to clamp this sacral anchor plate against the said bearing surface formed in the said second screw.

The equipment of the invention therefore comprises a sacral anchor plate able to be connected both to a first screw anchored to the first vertebra of the sacrum (S1), and to a second screw anchored to the second vertebra of the sacrum (S2), this sacral anchor plate additionally being connected to a part connecting the said rod to the said first screw, this connection—before positioning and clamping the said first nut—allowing polyaxiality and pivoting of the sacral connecting part relative to the anchor plate.

In practice, after placing in position the said first and second sacral anchoring screws, and the other bone anchoring members included in the equipment, the said link assembly is engaged on the connecting bar together with the other connecting parts of the equipment ; this connecting bar, thus equipped, is then placed in position on the bone anchoring members and the said link assembly is engaged on the shanks of the said first and second sacral anchor screws until it comes to bear upon the said bearing surfaces formed in these screws; the said second nut is then fully or partly clamped to allow this link assembly to take up a pre-position of the portion of the connecting bar extending at the vertebrae of the sacrum. The connecting bar is then rigidly affixed to the said anchor members included in the equipment; this affixing does not generate any stress on the fourth and fifth lumbar vertebrae or on the sacrum since the said first nut is not clamped and therefore the said sacral connecting part is able to tilt and pivot relative to the said sacral anchor plate. The said first nut is then clamped as is the second nut if this was not previously fully clamped, to terminate mounting; this clamping of the first nut therefore locks the connecting part in the position that this part has taken up subsequent to the shape and position of that portion of the connecting bar positioned opposite the vertebrae of the sacrum.

The equipment of the invention therefore allows a strong connection to be made to the vertebrae of the sacrum irrespective of the bone condition of the latter, and to obtain anchoring of the connecting bar to the sacrum without generating stresses on the fourth and fifth lumbar vertebrae or on the sacral anchor screws.

Preferably, each sacral anchor screw is polyaxial i.e. its threaded proximal shank articulates with the said threaded base portion.

Said screws facilitate the engaging of the said sacral anchor plate on the said threaded proximal shanks.

Preferably, the equipment of the invention comprises:
two sacrum anchor assemblies such as aforementioned, one being intended to be anchored onto the left of the sacrum relative to the axis of the spine and the other being intended to be anchored to the right of the sacrum relative to this same axis;
a cross-piece capable of linking the said second screws of these two sacrum anchor assemblies.

With this equipment, it is possible to obtain a perfectly rigid assembly with distribution of forces applied to the two sacrum anchor assemblies, in particular on the said second screws.

According to one preferred embodiment of the equipment, in this case, the cross-piece comprises openings at its ends, preferably oblong, and the said second nuts clamp this cross-piece between them and the sacral anchor plates.

Preferably, the equipment of the invention comprises at least one iliac anchor plate having a double-bended shape, namely comprising a first portion pierced with an orifice able to be engaged on the said shank of the said second screw, a second portion bent relative to the said first portion and a third portion bent relative to the said second portion, the said third portion or the said second and third portions being pierced with an orifice to receive an anchor screw in the iliac wing of the pelvis.

These iliac anchor plates can be used as needed to obtain even further reinforced anchoring of the equipment if required.

When the equipment comprises the said cross-piece and/or the said iliac anchor plate(s), the said sacral anchor plate(s), around said second orifices, advantageously comprise zones having an irregular surface e.g. knurled.

These zones allow perfect immobilisation of the said cross-piece and of the said iliac anchor plate relative to the sacral anchor plate, and hence allow the obtaining of a perfectly rigid assembly.

According to one preferred embodiment of the equipment according to the invention:
the said sacral connecting part is in two parts, including a main part comprising the said engaging orifices and a tubular part, for assembly onto the said sacral anchor plate, comprising the said bearing surface shaped as a portion of a sphere and forming a shoulder; and
the said means for assembling the said sacral connecting part onto the said sacral anchor plate comprise:

a groove arranged in the wall of the said main part delimiting the said orifice for engaging on the shank of the said first screw; and
press-fit teeth arranged in the said tubular assembling part and able to be press-fitted into this groove, the said sacral anchor plate being trapped between the said main part and the said shoulder of the tubular assembling part when this press-fitting is carried out.

BRIEF DESCRIPTION OF THE DRAWINGS

The invention will be better understood and other characteristics and advantages will become apparent with reference to the appended schematic drawing which as a non-limiting example illustrates one preferred embodiment of the equipment concerned.

FIG. 5 is a cross-sectional view of the link assembly along line V-V in FIG. 2 and in an exploded view;

FIG. 6 is a similar view to FIG. 5 in the assembled state and in a non-tilted position of the said connecting part relative to the said sacral anchor plate;

FIGS. 7 and 8 are similar views to FIG. 6 in tilted positions of the said connecting part relative to the said sacral anchor plate;

DESCRIPTION OF THE PREFERRED EMBODIMENTS

Figure 12:
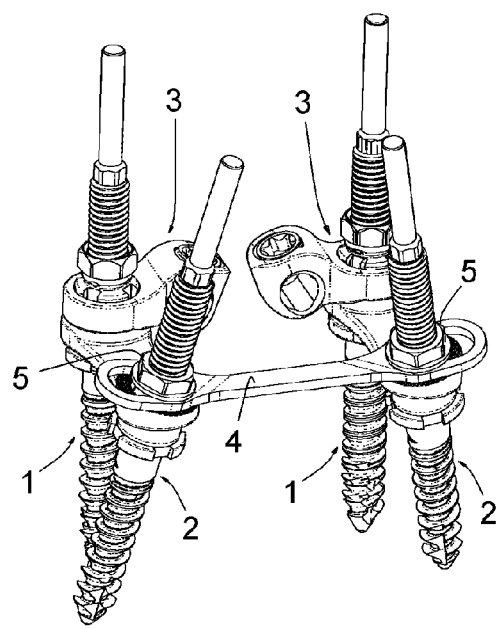
FIG. 12 is a perspective view of an implant assembly using the equipment of the invention, comprising two sacrum anchor assemblies and a cross-piece.
Figure 13:
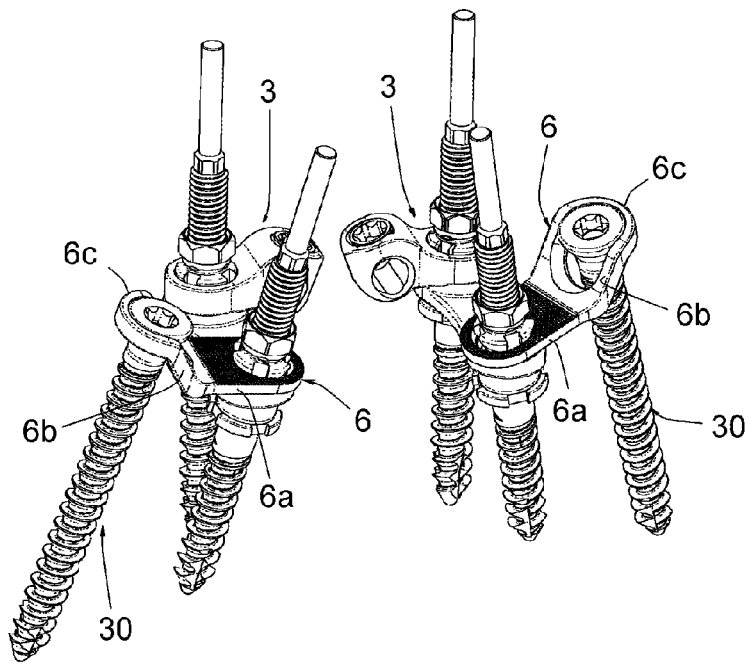
FIG. 13 is a perspective view of another implant assembly using the equipment of the invention, comprising two sacrum anchor assemblies and two iliac anchor plates.
Figure 14:
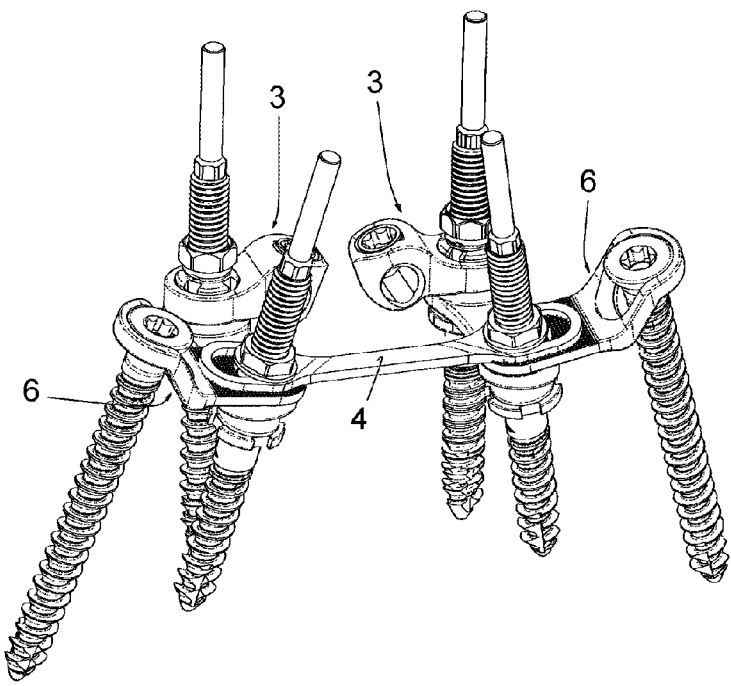
FIG. 14 is a perspective view of yet another implant assembly using the equipment of the invention, comprising both the cross-piece shown FIG. 12 and the two iliac anchor plates in FIG. 13.

FIGS. 12 to 14 illustrate three types of implant assembly allowed by the vertebral osteosynthesis equipment of the invention; the implant assembly illustrated in FIG. 12 comprises two pairs of sacral anchor screws 1, 2, two link assemblies 3, a cross-piece 4 and nuts 5; the implant assembly illustrated in FIG. 13 comprises the two pairs of screws 1, 2, the two link assemblies 3, the nuts 5 and a pair of iliac anchor plates 6; the implant assembly illustrated in FIG. 13 comprises the two pairs of screws 1, 2, the two link assemblies 3, the nuts 5 and both the cross-piece 4 and the pair of iliac anchor plates 6.

Figure 15:
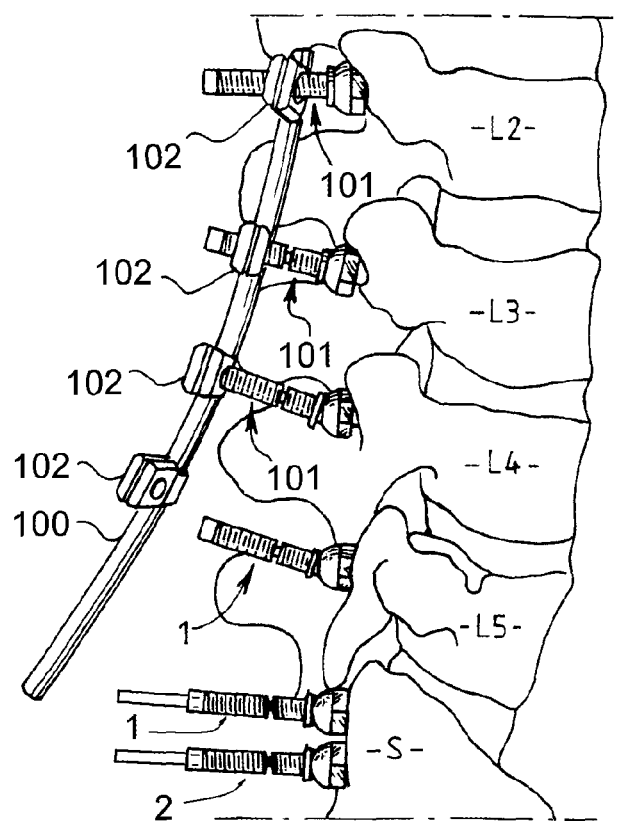
FIG. 15 is a side view of lumbar and sacrum vertebrae on which parts of the vertebral osteosynthesis equipment are implanted.

As shown on FIG. 15, the equipment also comprises two rigid connecting bars 100 (only one is shown) able to link several vertebrae (L2-L5 and S for second, third, fourth and fifth lumbar vertebrae and sacrum, respectively), bone anchoring members 101 (pedicle screws in the embodiment shown, but they can also be hooks) suitable for anchoring these connecting bars 100 to the vertebrae, and connecting parts 102 allowing the connecting bars 100 to be connected to these bone anchoring members 101. These different elements are known per se and on this account will not be described in detail. They may in particular be the pedicle screws, connecting bars and connecting parts described in WO 98/55038.

Each sacral anchoring screw 1, 2 comprises a threaded base portion 7 intended to be inserted in the corresponding vertebra, a bearing surface 8 shaped as a portion of a sphere and a threaded proximal shank 9, and is polyaxial i.e. its shank 9 articulates with respect to its threaded base portion 7. In manner known per se, this articulation is obtained by means of a spherical portion arranged at the distal end of the shank 9 and received in a spherical cavity centrally formed by the bearing surface 8, the wall forming the latter being crimped around this spherical portion. The principle of said screw is described in the above-mentioned document No WO 98/55038 to which reference can be made for more details.

Each screw 1 is intended to be implanted in the first vertebra of the sacrum and each screw 2 is intended to be implanted in the second vertebra of the sacrum; the two screws 1, 2 of a first sacrum anchor assembly are intended to be anchored onto the left of the sacrum relative to the axis of the spine, whilst the two screws 1, 2 of the second sacrum anchor assembly are intended to be anchored onto the right of the sacrum relative to this same axis.

Figure 1:
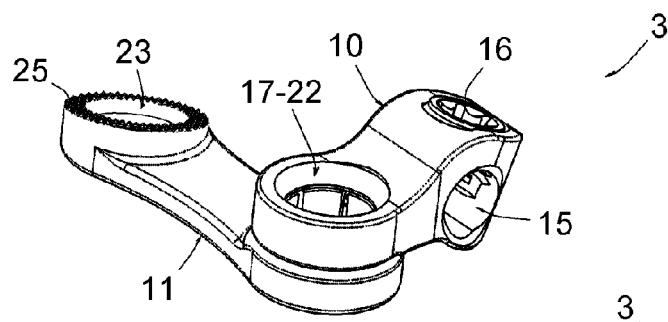
FIG. 1 is a perspective view of a link assembly contained in a sacrum anchor assembly that is part of this equipment, the equipment comprising two of these sacrum anchor assemblies.
Figure 2:
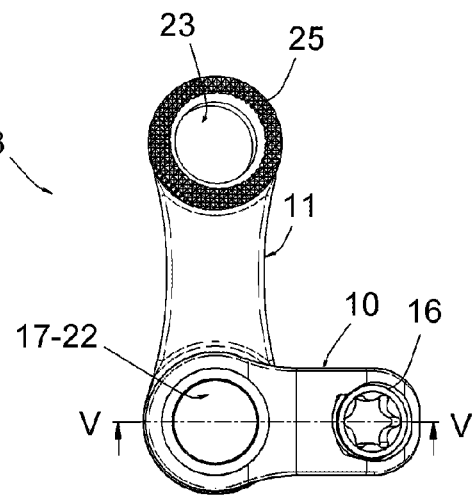
FIGS. 2 to 4 are overhead views of the link assembly, in three possible positions of a connecting part it includes, intended to connect with a sacral anchor plate it also includes.
Figure 3:
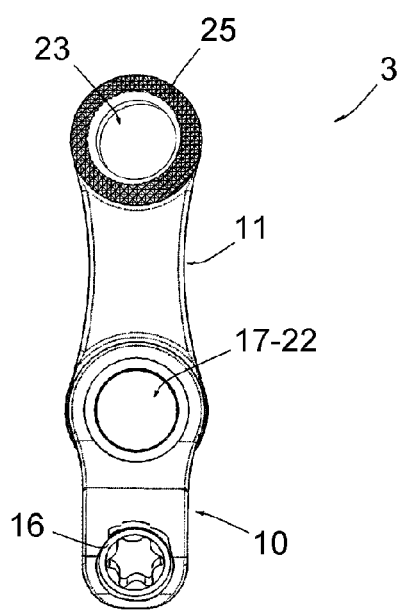
Figure 4:
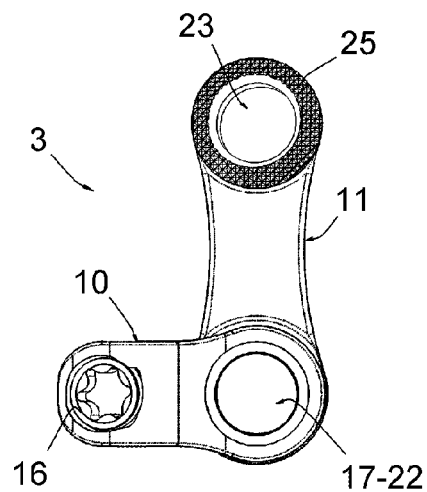

With more particular reference to FIGS. 1 to 4 and to FIGS. 6 to 8, it can be seen that each link assembly 3 comprises a sacral connecting part 10 and a sacral anchor plate 11 assembled onto each other, the connecting part 10 being connected to the plate 11 in a direction perpendicular to the plane of the views in FIGS. 2 to 4 (or from bottom upwards in FIGS. 6 to 8), being polyaxially mobile i.e. with possible multidirectional tilting (cf. FIGS. 7 and 8), and pivoting (cf. FIGS. 2 to 4) in relation to this plate 11.

As shown more particularly in FIG. 5, the connecting part 10 comprises a main part 10a and a tubular part 10b for mounting on the said plate 11.

The main part 10a comprises an orifice 15 for engaging on said connecting bar, a threaded plug or set screw 16 to clamp the rod in this orifice 15, to immobilise this rod relative to this part 10a, an orifice 17 for engaging on the shank 9 of the screw 1, and a groove 18 arranged in its wall delimiting this orifice 17 coaxially thereto. The portion of this orifice 17 intended to face the plate 19 is machined so as to form a recess 19 of conical or spherical shape allowing polyaxiality, as can be seen in FIGS. 6 to 8.

The tubular part 10b comprises a cylindrical part 10b1 and a part 10b2 shaped as a portion of a sphere. The cylindrical part 10b1 has a plurality of longitudinal slots leading to its edge opposite the part 10b2 and comprises an outer collar on its end opposite this same part 10b2, the assembly forming a plurality of press-fit teeth able to be press-fitted, or snapped, into the groove 18 as can be seen by comparison between FIGS. 5 and 6. The part 10b2 outwardly forms a shoulder 20 having a surface in the shape of a portion of a sphere which, when press-fitting has been carried out, allows trapping of the plate 11 between the main part 10a and this shoulder, as can be seen in FIGS. 6 to 8. The part 10b2 inwardly forms a bearing surface 21 shaped as a portion of a sphere intended to bear upon the said bearing surface 8 of a screw 1. This bearing surface 21 has a slightly larger radius than the bearing surface 8 and is of shorter height than the latter, which means that polyaxial clearance of the part 10 relative to this surface 8 is possible over about fifteen degrees either side of the neutral position shown in FIG. 6, as can be seen in FIGS. 7 and 8.

The plate 11 comprises a first orifice 22 intended to engage on the shank 9 of a screw 1 and a second orifice 23 intended to engage on the shank 9 of a screw 2, the orifices 17 and 22 being coaxial after assembling the part 10 and the plate 11. The orifice 22, in its part intended to lie opposite the part 10a, forms a bearing surface 24 shaped as a portion of a sphere, able to receive the shoulder 20 in assembled position with possible sliding. The second orifice 23 is surrounded by a surface 25 which can be slightly angled relative to the plane of this plate 11, as can be seen in FIG. 1, to obtain a corresponding anatomical angle between the plate 11 and the bearing surface 8, and this surface 25 also being knurled for non-sliding reception of a nut 5 or of the cross-piece 4 or of the iliac anchor plate 6 as described below.

The nuts 5, in the illustrated example, are of the type having a lower part which engages in an orifice 22 or 23 and a hexagonal upper part used for handling.

Figure 9:
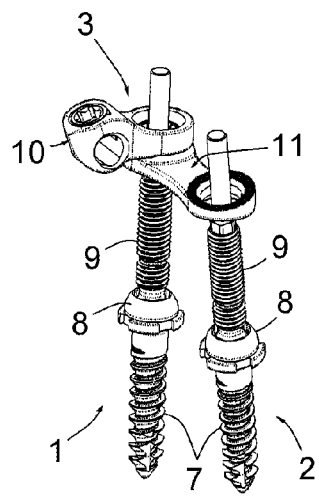
FIGS. 9 to 11 are perspective views of a sacrum anchor assembly comprising two sacral anchor screws, a link assembly as in FIGS. 1 to 7 and two nuts, showing three successive steps for placing the link assembly in position on the screws.
Figure 10:
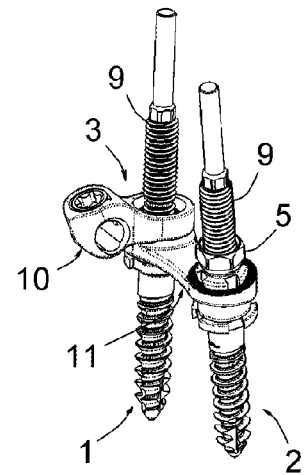
Figure 11:
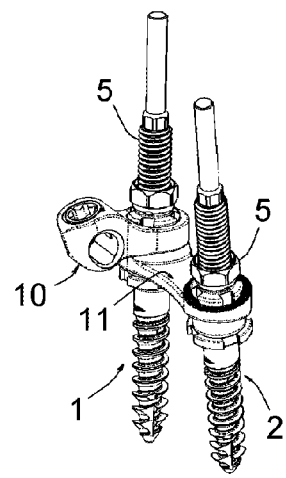

In practice, as can be understood with reference to FIGS. 9 to 11, after placing in position a first screw 1 and a second screw 2 respectively in the first and second vertebrae of the sacrum, and other bone anchoring members provided in the equipment in the other vertebrae to be treated, a link assembly 3 is engaged on the connecting bar (not illustrated in FIGS. 9 to 14 for reasons of clarity); the other connecting parts included in the equipment are also engaged on this rod; the connecting bar thus equipped is then placed in position on the said bone anchoring members, and the link assembly 3 is engaged on the shanks 9 of the screws 1 and 2 (FIG. 9) until it comes to bear upon the bearing surfaces 8 formed in these screws; a nut 5 is then fully or party clamped on the shank 9 of the screw 2 (FIG. 10) to allow the link assembly 3 to obtain pre-positioning of the portion of the connecting bar extending at the vertebrae of the sacrum. The connecting bar is then rigidly affixed to the said anchor members included in the equipment; this affixing does not generate any stress on the fourth and fifth lumbar vertebrae or on the sacrum having regard to the possible tilting and pivoting of the connecting part 10 relative to the plate 11. A nut 5 is then placed in position and clamped (FIG. 11) to complete mounting the assembly, thereby locking the part 10 in the position that this part comes to assume as imposed by the position of the connecting bar.

FIG. 12 shows that the cross-piece 4 can be used to connect the left sacral anchor assembly to the right sacral anchor assembly at the two screws 2. The cross-piece 4 comprises oblong openings at its ends and the nuts 5 of these screws 2 clamp this cross-piece between them and the sacral anchor plates 11.

FIG. 13 shows that each iliac anchor plate 6 has a double-bend shape, namely it comprises a first portion 6a pierced with an orifice able to be engaged on the shank 9 of a screw 2, a second portion 6b bent relative to the first portion 6a, and a third portion 6c bent relative to the portion 6b. The third portion 6c and the second portion 6b are pierced with an orifice to receive an anchor screw 30 in the iliac wing of the pelvis. The above-mentioned tilting of the surface 24 allows adequate orienting of the plate 6.

The two iliac anchor plates 6 can be used according to needs, to obtain even further reinforced anchoring of the equipment if required.

FIG. 14 shows the simultaneous use of the cross-piece 4 and the plates 6, the cross-piece being positioned above portions 6a of the plates 6.

As is apparent from the foregoing, the invention provides vertebral osteosynthesis equipment which, compared with approved equipments in the prior art, has the following determinant advantages:

allows strong anchoring to the sacrum to be obtained, including if bone is of poor quality;

eliminates the risk of applying undesirable stress on the fifth and fourth lumbar vertebrae.

The invention has been described above with reference to one embodiment given as an example. It is evidently not limited to this embodiment but encompasses all other embodiments covered by the appended claims.

What is claimed is:

1. A vertebral osteosynthesis equipment comprising:
   at least one connecting bar configured to link several vertebrae;
   bone anchoring members configured to anchor the at least one connecting bar onto the several vertebrae;
   connecting parts configured to connect the at least one connecting bar to to the bone anchoring members; and
   at least one sacrum anchor assembly, each sacrum anchor assembly comprising:
      two sacral anchor screws, a first screw of the two sacral anchor screws configured to be implanted in a first vertebra of a sacrum and a second screw of the two sacral anchor screws configured to be implanted in a second vertebra of the sacrum, each screw of the two sacral anchor screws comprising a threaded base portion configured to be inserted in a corresponding vertebra, a sacral anchor bearing surface, and a threaded proximal shank, wherein a shape of said sacral anchor bearing surface of the first screw is a portion of a sphere;
      a link assembly comprising:
         a sacral connecting part comprising a first orifice configured to engage on said at least one connecting bar, a second orifice configured to engage on the shank of said first screw, and a sacral connecting bearing surface shaped as a portion of a sphere configured to bear upon the sacral anchor bearing surface formed in the first screw, the sacral connecting bearing surface being obtained via polyaxiality, such that the sacral connecting part has multi-directional tilting relative to the first screw;
         a sacral anchor plate comprising a first orifice and a second orifice, the distance between the first orifice and the second orifice being such that the first orifice is engageable on the shank of the first screw and the second orifice is engageable on the shank of the second screw;
         means for assembling the sacral connecting part to the sacral anchor plate, the assembling being such that the second orifice of the sacral connecting part lies coaxial to the first orifice of the sacral anchor plate, the sacral connecting part being connected to the sacral anchor plate in a direction parallel to an axis of the first orifice of the sacral anchor plate and the second orifice of the sacral connecting part, and the sacral connecting part being configured to pivot relative to the sacral anchor plate along the same axis;
         two nuts, a first nut of the two nuts configured to be screwed onto the shank of the first screw and to bear against the sacral connecting part so as to clamp the sacral connecting part against the sacral anchor bearing surface formed in the first screw, such that there is tilt and pivot immobilization of the sacral connecting part relative to the sacral anchor plate, and the second nut of the two nuts configured to be screwed onto the shank of the second screw and to bear against the sacral anchor plate so as to clamp the sacral anchor plate against the sacral anchor bearing surface formed in the second screw.

2. The vertebral osteosynthesis equipment according to claim 1, wherein each sacral anchor screw of the two sacral anchor screws is polyaxial, such that the threaded proximal shank of each screw articulates with the threaded base portion of each screw.

3. The vertebral osteosynthesis equipment according to claim 1, wherein:
   a first of the at least one sacrum anchor assemblies is configured to be anchored onto a left of the sacrum relative to an axis of a spine and a second of the at least one sacrum anchor assemblies is configured to be anchored onto a right of the sacrum relative to the same axis of the spine;
   a cross-piece configured to link the two screws of the first and second at least one sacrum anchor assemblies.

4. The vertebral osteosynthesis equipment according to claim 3, wherein the cross-piece comprises oblong openings at its ends and wherein the two nuts clamp the cross-piece between the two nuts and the sacral anchor plate.

5. The equipment according to claim 4, wherein the said sacral anchor plates, around said second orifices, comprise zones having an irregular surface e.g. knurled.

6. The vertebral osteosynthesis equipment according to claim 1, further comprising at least one iliac anchor plate having a double-bended shape, the at least one iliac anchor plate comprising a first portion pierced with an orifice configured to be engaged on the shank of the second screw, a second portion bent relative to the first portion and a third portion bent relative to the second portion, the second and third portions being pierced with an orifice to receive an anchor screw in an iliac wing of a pelvis.

7. The equipment according to claim 1, wherein:
   the said sacral connecting part is in two parts, including a main part comprising the said engaging orifices and a tubular part, for assembly onto the said sacral anchor plate, comprising the said bearing surface shaped as a portion of a sphere and forming a shoulder; and
   the said means for assembling the said sacral connecting part onto the said sacral anchor plate comprise:
      a groove arranged in the wall of the said main part delimiting the said orifice for engaging on the shank of the said first screw; and
      press-fit teeth arranged in the said tubular part and able to be press-fitted into this groove, the said sacral anchor plate being trapped between the said main part and the said shoulder of the tubular part when this press-fitting is carried out.

* * * * *